United States Patent [19]

Wakamatsu et al.

[11] Patent Number: 4,835,301

[45] Date of Patent: * May 30, 1989

[54] PROCESS FOR PRODUCING STABLE α-L-ASPARTYL-L-PHENYLALANINE METHYL ESTER

[75] Inventors: Hidetoshi Wakamatsu, Shin-nanyo; Shigeaki Irino, Yamaguchi; Tsuneo Harada; Akira Tokuda, both of Shin-nanyo; Kiyotaka Oyama, Hikari, all of Japan

[73] Assignee: Toyo Soda Manufacturing Co., Ltd., Yamaguchi, Japan

[ * ] Notice: The portion of the term of this patent subsequent to Mar. 7, 2006 has been disclaimed.

[21] Appl. No.: 83,802

[22] Filed: Aug. 11, 1987

[30] Foreign Application Priority Data

Aug. 13, 1986 [JP] Japan .................................. 61-188661

[51] Int. Cl.⁴ ............................................. C07C 101/02
[52] U.S. Cl. ....................................................... 560/41
[58] Field of Search ........................... 560/41; 530/801; 426/548; 34/10, 26, 31

[56] References Cited

U.S. PATENT DOCUMENTS 4,579,747 9/1986 Sugiyama et al. .................. 426/548

FOREIGN PATENT DOCUMENTS

| 57-42623 | 4/1982 | Japan . |
| 59-95862 | 5/1984 | Japan . |
| 59-172444 | 9/1984 | Japan . |
| 60-37949 | 7/1985 | Japan . |

OTHER PUBLICATIONS

Perry et al, *Chemical Engineers' Handbook*, 5th Ed., McGraw-Hill, New York, pp. 20-24 to 20-16 (1973).
"Application Potential for Aspartame in Low Calorie and Dietetic Foods", In Low Calorie and Special Dietary Foods, pp. 59-114, CRC Press 1978, CFR 21, Food and Drugs revised as of Apr. 1, 1981.

*Primary Examiner*—Bruce D. Gray
*Attorney, Agent, or Firm*—Nixon & Vanderhye

[57] ABSTRACT

A process for producing stable α-L-aspartyl-L-phenylalanine methyl ester, which comprises heat-treating crystals of α-L-aspartyl-L-phenylalanine methyl ester having a water content of from 5 to 15% by weight based on wet crystals, at a temperature of higher than 50° C. and lower than 80° for at least 30 minutes.

7 Claims, No Drawings

PROCESS FOR PRODUCING STABLE α-L-ASPARTYL-L-PHENYLALANINE METHYL ESTER

The present invention relates to a process for producing α-L-aspartyl-L-phenylalanine methyl ester (hereinafter referred to as Aspartame) having excellent storage stability.

Aspartame has two types of crystal forms i.e. I and II types. The I type crystals are hygroscopic, and they are likely to undergo color change or decomposition during storage. Whereas, the II type crystals are less hygroscopic, and it has been taught that they have good flowability and storage stability.

Heretofore, a method has been proposed wherein wet Aspartame crystals are dried at a temperature of at least 80° C. to obtain the II type crystals of Aspartame (Japanese Unexamined Patent Publications Nos. 172441/1984 and 37949/1985), or a method for preparing granules has been known in which dried II type crystals are hydrated to have a water content of from 35 to 45% by weight, followed by extrusion granulation and drying again (Japanese Unexamined Patent Publication No. 95862/1984).

In the conventional processes, crystals are dried at a high temperature to obtain the II type crystals, and it is likely that a decomposition product of Aspartame i.e. a diketopiperadine derivative, is likely to form. Further, in order to obtain granules, a dried product of the II type crystals of Aspartame is required to be hydrated once, followed by granulation and drying again, such being disadvantageous from the viewpoint of the process control and a cost for energy.

It is an object of the present invention to solve such problems and to provide a process for producing Aspartame having excellent storage stability without requiring high temperature drying and redrying as required in the conventional processes.

The present inventors have conducted extensive research to solve the above-mentioned problems, and have found it possible to obtain stable II type crystals of Aspartame by heating I type crystals of Aspartame in a specific range of the water content without requiring high temperature drying or redrying.

Thus, the present invention provides a process for producing stable α-L-aspartyl-L-phenylalanine methyl ester, which comprises heat-treating crystals of α-L-aspartyl-L-phenylalanine methyl ester having a water content of from 5 to 15% by weight based on wet crystals, at a temperature of higher than 50° C. and lower than 80° C. for at least 30 minutes.

Now, the present invention will be described in detail with reference to the preferred embodiments.

The wet Aspartame crystals prior to drying in accordance with the process of the present invention may be prepared by any precipitation and separation methods. There is no restriction as to the method for the preparation of the wet Aspartame crystals.

The wet Aspartame crystals thus obtained may or may not be treated by a granulator. When it is treated by a granulator, any type of granulator such as an extrusion type granulator or a compression type granulator may be employed. When the wet Aspartame crystals are treated by extrusion by means of an extrusion type granulator, granules of a cylindrical shape can be obtained by passing the wet Aspartame crystals through a screen having a mesh size of from 0.1 to 10.0 mm in diameter. It is preferred to pass the wet crystals through a screen having a mesh size of from 1.0 to 4.0 mm in diameter.

Such wet Aspartame crystals usually contain far more than 15% by weight of water. Therefore, the wet crystals are firstly dried to a water content of from 5 to 15% by weight. There is no particular restriction as to the temperature and the drying method for the drying of wet Aspartame crystals (which may or may not be granulated) to a water content of from 5 to 15% by weight based on wet crystals. For example, the drying machine may be of a usual type, but is preferably an air stream drier or a fluidized-bed drier whereby the retention time is long. If the temperature is too high, a diketopiperadine derivative as a decomposition product of Aspartame is likely to form. Therefore, the drying is preferably conducted at a temperature of lower than 80° C. The wet Aspartame crystals having a water content of from 5 to 15% by weight is then heat-treated at a temperature of higher than 50° C. and lower than 80° C. The heat treatment may be conducted by an air stream drier or a fluidized bed drier. However, it is preferred to conduct the treatment in a sealed container for from 30 minutes to 48 hours. The heat treatment is continued until the crystal form of Aspartame is changed to the stable crystal form, and the heat treatment time is dependent on the water content and the temperature. Once the change to the stable Aspartame has been completed, further drying can be conducted at any temperature within a range where Aspartame udergoes no substantial decomposition. Thus, it is possible to obtain dry Aspartame having excellent stability.

Now, the present invention will be described in further detail with reference to Examples. However, it should be understood that the present invention is by no means restricted to such specific Examples.

In the Examples, the ratio of II type crystals (the ratio (%) of the II type crystals to the total amount of the I and II type crystals) was determined as follows: Standard samples of the I and II type crystals were mixed at various ratios, and calibration curve was prepared based on the ratios in the strength of the specific peaks at the respective X-ray diffraction angles (2 θ) of 4.4° (I type) and 5.0° (II type). Then, the ratio of the II type crystals was determined by compairing the strength ratio of each sample with the calibration curve.

Further, in the Examples, the hygroscopicity of Aspartame was determined by storing a sample in an air at a temperature of 25° C. under a humidity of 78%, and the storage stability was determined by placing from 2 to 3 g of Aspartame in a sealed container (20 ml), which was then stored in a constant temperature tank of 55° C. and measuring the water content and the diketopiperadine content after an expiration of a predetermined period of time.

EXAMPLE 1

Wet Aspartame crystals (5 kg) obtained by solid-liquid separation by means of a centrifugal separator, was extruded through a screen having a mesh size of 2.0 mm in diameter, and granulated. The wet granules (60 g) thus obtained were dried in an air stream drier by means of a hot air stream of 60° C. to a water content of 10.1% by weight. The granules (5 g) were placed in a sealed container and heat-treated at 60° C. for about 1 hour, and then dried in an air stream drier by means of a hot air stream of 60° C. (Yield: 4.6 g, Example 1)

On the other hand, for the purpose of comparison, the above wet granules (60 g) were dried under reduced pressure at 40° C. for 6 hours. (Yield: 24.6 g, Comparative Example 1)

The results of the storage stability and the hygroscopicity are shown in Table 1.

TABLE 1

| Number of Example or Comparative Example | Ratio of II type crystals | Hygroscopicity Water content (%) | | Storage stability Content of diketopiperadine (%) | |
|---|---|---|---|---|---|
| | | Immediately after drying | After 24 hours test | Immediately after drying | After 79 days test |
| Example 1 | 100 | 2.0 | 5.4 | 0.20 | 0.94 |
| Comparative Example 1 | 0 | 2.3 | 8.7 | 0.23 | 1.21 |

EXAMPLES 2 to 12

Wet Aspartame granules (250 g) prepared in the same manner as in Exmaple 1 were dried at 60° C. under reduced pressure to obtain granules having water contents of (1) 19.5% by weight (20 g), (2) 15.4% by weight (17 g), (3) 10.1% by weight (23 g), (4) 5.5% by weight (18 g) and (5) 2.3% by weight (20 g ), respectively. They were respectively treated by heating at various temperatures in sealed containers, followed by drying at 60° C. under reduced pressure, to obtain dry Aspartame products having water contents of (1) 2.1% by weight (from 19.5% by weight), (2) 1.5% by weight (from 15.4% by weight), (3) 1.8% by weight (from 10.1% by weight) and (4) 2.0% by weight (from 5.5% by weight), respectively. The increases in the water contents of the dry Aspartame products during the storage were measured, and the results are shown in Table 2.

As is apparent from the foregoing description, according to the present invention, it is possible to obtain dry Aspartame having excellent storage stability without necessity of high temperature drying, or reducing which is disadvantageous from the viewpoint of the process control and costs for energy.

The dry Aspartame product having excellent storage stability of the present invention is particularly useful when it is used as a table sweetener in the form of granules or tablets together with sugars or other substances.

We claim:

1. A process for producing stable α-L-aspartyl-L-phenylalanine methyl ester, which process comprises heat-treating crystals of α-L-aspartyl-L-phenylalanine methyl ester having a water content of from 5 to 15% by weight based on wet crystals, at a temperature of at least 50° C. but lower than 80° C. for at least 30 minutes, to produce α-L-aspartyl-L-phenylalanine methyl ester crystals in which the ratio of II type crystals is at least 78%.

2. The process according to claim 1, wherein the heat treatment is conducted within 48 hours.

3. The process according to claim 1, wherein the crystals of α-L-aspartyl-L-phenylalanine methyl ester

TABLE 2

| Number of Example or Comparative Example | Heat treatment | | Water content at the initiation of heat treatment (%) | Ratio of II type crystals (%) | Hygroscopicity Water content increase (%) (After 48 hours test) |
|---|---|---|---|---|---|
| | Temperature (°C.) | Time (hr) | | | |
| Comparative Example 2 | 40 | 17 | 5.5 | 0 | 9.9 |
| Example 2 | " | " | 10.1 | 45 | 8.0 |
| Example 3 | 50 | 3 | 10.1 | 78 | 5.3 |
| Example 4 | " | 17 | 5.5 | 45 | 7.6 |
| Example 5 | " | " | 10.1 | 100 | 4.0 |
| Comparative Example 3 | " | " | 19.5 | 0 | 9.5 |
| Example 6 | 60 | 1 | 10.1 | 100 | 3.7 |
| Example 7 | " | 3 | 5.5 | 100 | 4.1 |
| Example 8 | " | 3 | 10.1 | 100 | 4.0 |
| Comparative Example 4 | " | 3 | 15.4 | 0 | 9.8 |
| Example 9 | 70 | 1 | 5.5 | 100 | 3.8 |
| Example 10 | " | 1 | 10.1 | 100 | 3.8 |
| Comparative Example 5 | " | 1 | 15.4 | 10 | 9.0 |
| Example 6 | " | 16 | 2.3 | 0 | 9.5 |
| Example 11 | " | " | 5.5 | 100 | 3.8 |
| Example 12 | " | " | 10.1 | 100 | 3.8 |
| Comparative Example 7 | " | " | 19.5 | 0 | 9.0 |
| Example 8 | 80 | 17 | 2.3 | 10 | 9.1 |
| Example 9 | " | " | 19.5 | 8 | 9.5 |

EXAMPLE 13

Wet Aspartame crystals (80 kg) prepared in the same manner as in Example 1, were dried in a conical drier as a sealed container at 60° C. under reduced pressure, to a water content of 9.4% by weight. Then, the heat treatment was conducted at 60° C. for 1 hour, followed by drying again under reduced pressure for 3 hours, to obtain 32.5 kg of a dried product of stable Aspartame (composed of 100% of II type crystals) having a water content of 1.8%.

having a water content of from 5 to 15% by weight are granulated by a granulator prior to the heat treatment.

4. The process according to claim 3, wherein the granules have a diameter of from 0.1 to 10.0 mm.

5. The process according to claim 1, wherein the heat treatment is conducted in a sealed container.

6. The process according to claim 1, wherein the heat treatment is conducted in an air stream drier.

7. The process according to claim 1, wherein the heat treatment is conducted in a fluidized-bed drier.

* * * * *